United States Patent
Quinlan et al.

(10) Patent No.: US 8,354,129 B2
(45) Date of Patent: Jan. 15, 2013

(54) VITAMIN CONTAINING PRODUCT

(75) Inventors: Paul Thomas Quinlan, Sharnbrook (GB); Cees Vermeer, Maastricht (NL)

(73) Assignee: Nattopharm ASA, Oslo (NO)

( * ) Notice: Subject to any disclaimer, the term of this patent is extended or adjusted under 35 U.S.C. 154(b) by 1424 days.

(21) Appl. No.: 09/850,804

(22) Filed: May 8, 2001

(65) Prior Publication Data

US 2002/0015762 A1 Feb. 7, 2002

(30) Foreign Application Priority Data

May 12, 2000 (EP) .................................. 00303995

(51) Int. Cl.
*A23L 1/302* (2006.01)
(52) U.S. Cl. .......... 426/72; 426/580; 426/589; 426/590; 426/615; 526/160
(58) Field of Classification Search .................... 426/72, 426/580, 615, 589, 590; 526/160, 339
See application file for complete search history.

(56) References Cited

U.S. PATENT DOCUMENTS

| 3,949,098 A | 4/1976 | Bangert |
| 5,180,747 A | 1/1993 | Matsuda et al. |
| 6,093,425 A | 7/2000 | Kamarei |

FOREIGN PATENT DOCUMENTS

| DE | 19955607 | 7/2001 |
| EP | 0613877 A1 | 7/1994 |
| EP | 0 679 394 A2 | 2/1995 |
| EP | 1 153 548 A1 | 11/2001 |
| GB | 2 180 747 A | 8/1987 |
| WO | 99/00135 | 1/1999 |
| WO | WO 03013420 A2 | 2/2003 |

OTHER PUBLICATIONS

European Search Report dated May 28, 2001.
L.J. Schurgers, *Journal of Nutritional & Environmental Medicine* (1999) "Nutritional Intake of Vitamins $K_1$ (Phylloquinone) and $K_2$ (Menaquinone) in The Netherlands", pp. 115-122—mentioned on p. 2 of the specification.
Girjsbers, Birgit LM et al., *British Journal of Nutrition* (1996), "Effect of food composition on vitamin K absorption in human volunteers", 76, pp. 223-229—mentioned on p. 3 of the specification.
Yoshio Suzuki, *Nutrition Research*, 1997, "Production of Hen's Eggs Rich in Vitamin K" vol. 17, No. 10, pp. 1607-1615—mentioned on p. 3 of the specification.
Ichiro Iwamoto, *Maturitas* 31, A longitudinal study of the effect of vitamin $K_2$ on bone mineral density in postmenopausal women a comparative study with vitamin $D_3$ and estrogen-progestin therapy, (1999), pp. 161-164.
Morishita et al., *Journal Diary Sci.*, 1999, "Production of Menaquinones by Lactic Acid Bacteria", 82, pp. 1897-1903.
J.M. Geleijnse, et al., Dietary Intake of Vitamin K-2 (Menaquinone) May Protect Against Ischaemic Heart Disease: The Rotterdam Study (To be published).
J.M. Geleijnse, et al., "Inverse Association of Dietary Vigamin K-2 Intake with Cardiac Events and Aortic Atherosclerosis: The Rotterdam Study"; Citation: Supplement to the journal Thrombosis and Haemostasis, Jul. 2001 (ISSN 0340-6245) Abstract: P473.
Kawashima et al "Effects of Vitamin K2 (Menatetrenone) on Atherosclerosis and Blood Coagulation in Hypercholesterolemic Rabbits" Jpn. J. Pharmacol, vol. 75, pp. 135-143 (1997).
Cees Vermeer et al, "Role of K vitamins in the regulation of tissue calcification", J Bone Miner Metab, vol. 19, pp. 201-206 (2001).
MH Beers, "The Merck Manual of Diagnosis and Therapy" 1999, Merck Research Laboratories, Whitehouse Station, XP002260508, pp. 1654-1658.
M. Eder: "Lehrbuch der Allgemeinin Pathologie und der Pathologischen Anatomie", 1984, Springer Verlag, Heidelberg XP002260509, pp. 345-351.
International Search Report.
Oxenham, et al. "Cardiovascular Aging and Heart Failure", The European Journal of HeartFailure, vol. 5, pp. 427-434, (2003).
British Patent Office Search Report.
Mönckeberg's Sclerosis Evidence for Smooth Muscle Cell-Mediated Vascular Calcification, Circulation, Nov. 23, 1999, pp. 2168-2176.
Shanahan, et al. "Medial Localization of Mineralization-Regulating Proteins in Association With Mönckeberg's Sclerosis" Evidence for Smooth Muscle Cell-Mediated Vascular Calcification, Circulation, Nov. 23, 1999, pp. 2168-2176.
M.E. Rosenfeld, "An overview of the evolution of the atherosclerotic plaque: from fatty streak to plaque rupture and thrombosis", Z Kardio 89; Supp 7, VII/2-VII6 (2000) ©Steinkopff Verlag 2000.

*Primary Examiner* — Helen F Heggestad

(74) *Attorney, Agent, or Firm* — Rothwell, Figg, Ernst & Manbeck, P.C.

(57) ABSTRACT

A food product comprising menaquinone at a level of 50 to 5,000 µg per 100 g of product.

18 Claims, No Drawings

VITAMIN CONTAINING PRODUCT

FIELD OF INVENTION

The present invention relates to products comprising menaquinone. In particular the invention relates to food products comprising menaquinone, whereby menaquinone has preferably been added to the food products, and the use of these products for promoting the health of human beings, in particular bone and cardiovascular health.

BACKGROUND OF THE INVENTION

Menaquinone, also known as vitamin k2 is produced by bacteria and found in certain animal tissue such as liver. The structure of menaquinone is given in Figure 1. In this figure n indicates the number of unsaturated isoprenoid residues, generally being between 1 and 25.

Fig. 1 Vitamin $K_2$ (menaquinone)

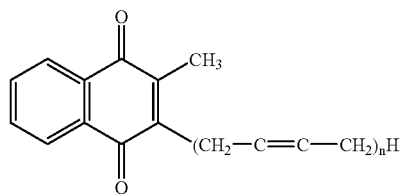

It is known that protein rich products such as meat, fish, cheese, eggs and other dairy products as well as fermented soy-bean contain some menaquinone. Table 1 indicates for some of these products the amounts of MK-4 (n=4) or MK-n (n is greater than 4) for certain food products.

TABLE 1

| Food product | Vit K2 concentration in μg/100 g or μg/100 ml MK-4 | Vit K2 concentration in μg/100 g or μg/100 ml MK-n |
|---|---|---|
| Meat | 1–30 | — |
| Fish | 0.1–2 | 0.1–2 |
| Natto | — | 900–1200 |
| Cheese | 0.5–10 | 40–80 |
| Other dairy | 0.2–15 | 0–35 |
| Eggs | 10–25 | — |

L. J Schurgers in Journal of Nutritional & Environmental medicine (1999) 9, 115-122 recommends a significant increase of the daily intake of menaquinone to a level of 45 μg per day. However to achieve this amount it will be necessary to adapt the daily diet and for example to increase the amount of cheese to be eaten to say to at least 100 g of cheese per day. For a great number of consumers however high intakes of products like cheese is not acceptable because it either does not fit in their desired diet (they do not like cheese, or do not take animal proteins) or it may be bad for overall health for example cheese has a high caloric content and a high degree of saturated fatty acids that promote cardiovascular disease).

Another possibility to increase the level of menaquinone in the diet is to increase the intake of a fermented soy product (natto) which typically contains 900-1200 μg per 100 g. Sometimes however the use of natto as a food ingredient is less preferred because it is very difficult to process and often provides a less-desired taste to the food products.

For this reason it has been proposed to add menaquinone as an additive to food products so as to increase the menaquinone intake per day.

Gijsbers, Birgit L M et al, British Journal of Nutrition (1996), 76, 223-229 reported that intake of 5 g butter to which 800 μg MK-4 had been added (equivalent to 16 mg MK-4 per 100 g butter) increased the MK-4 levels in blood serum. Yoshio Suzuki, Nutrition Research, 1997, Vol 17, No 10, pp 1607-1615, suggested with regard to prevention and treatment of HDN (haemorrhagic disease of newborn) to improve the fetal vitamin K nutritional status by including vitamin K as a maternal food supplement. It was taught that MK-4 levels in hen's eggs can be increased to about 130 μg per 100 g egg yolk (50 μg per egg) if hen are fed for 30 days on a menadione enriched diet.

Up till now however it was believed that menaquinone when used as a food additive has to be used at relative high levels say 100,000 μg per 100 g product in order to be effective to promote bone or cardiovascular health. For example in the Chem Abstract of JP 11/127816 a beverage is described which contains 0.1 part menaquinone on 100 parts of product, said menaquinone level corresponding to 100,000 μg per 100 g of product.

The purpose of the present invention is to provide food products with an effective level of menaquinone, said food products being easy to manufacture at a reasonable cost and whereby the level is chosen such that the food product is effective to promote bone health or cardiovascular health.

Surprisingly it has now been discovered that a food product comprising a menaquinone as an additive in a specific amount can be used for promoting the health of human beings, in particular cardiovascular and bone health. Especially it has been found that the amount of menaquinone per serving or per 100 g of product can be kept at a significantly lower level than proposed till now for food products, while still providing the desired health effects.

Accordingly in a first aspect the invention relates to a food product comprising menaquinone at a level of 50 to 5,000 μg per 100 g of product. In a second embodiment the invention relates to a food product comprising menaquinone at a level of 50 to 5,000 μg per serving. If the menaquinone is a MK-n menaquinone, then food products that naturally comprise these levels of menaquinone such as some cheeses and natto are excluded from the scope of the invention.

In another preferred embodiment of the invention the food product is not a highly proteinaceous food product such as meat, fish, dairy product or eggs.

DETAILED DESCRIPTION OF THE INVENTION

Osteoporosis is a growing problem in modern society, especially for women of middle age or older. Vitamin K2 (menaquinone) has been proposed as a suitable ingredient in pharmaceutical compositions to prevent osteoporosis, and to promote cardiovascular health. See Ichiro Iwamoto in Maturitas 31 (1999) 161-164. Typical levels for these pharmaceutical compositions are 45,000 μg per day. See also WO 99/00135 where the amount of vitamin K in a pharmaceutical composition for prevention and treatment of osteoporosis can be reduced to 5-5000 μg per day if 5-5000 μg of vitamin D is present in the composition.

The present inventions provide food products that can be part of the normal daily diet, wherein said food products comprise an effective amount of menaquinone.

Surprisingly it has been found that there is no need for the levels of menaquinone as suggested so far to get the desired health effect. More specifically it has been found that levels in food products of less than 5 mg per day, for example from 50 to 5,000 µg per day, preferably 100 to 1000 µg per 100 g of product or per serving of the food product are already sufficient to get the health effect.

The higher levels are most appropriate in foods that may be consumed less frequently (once or twice per week) or in foods where bioavailability of the menaquinone is expected to be lower, and the lower levels are most appropriate for foods that may be consumed several times per day or in foods where bioavailability of the menaquinone is expected to be higher.

Preferred menaquinone levels are from 60 to 600 µg per 100 g product or per serving, more preferred 75 to 400 µg, most preferred 100 to 200 µg per 100 g of product or per serving.

The menaquinone for use in food products of the invention may be obtained from any suitable source. For example it may be obtained from a fermented soy product (natto which typically contains 900-1200 µg per 100 g. Sometimes however the use of natto as a food ingredient is less preferred because it is very difficult to process and often provides a less-desired taste to the food products.

Alternatively the menaquinone may be synthetically prepared. Especially preferably the menaquinone may be prepared by microbial production. These menaquinone products have the advantage that they have a controlled constant quality, can be obtained at reasonable costs and can easily be incorporated in food products without negatively affecting the taste.

Particularly advantageous for use in products of the invention are menaquinone having an average number of side groups of from 2 to 10, more preferred from 3 to 5, more preferred about 4.

Several food products may be used for the incorporation of menaquinone, for example meal replacers, ice-cream, sauces, dressing, spreads, bars, sweets, snacks, cereals, beverages etc.

Table 1 indicates a number of products in which menoquinone may be incorporated and a typical serving size.

TABLE 1

| Product | Serving size |
|---|---|
| Margarine | 15 g |
| ice-cream | 150 g |
| Dressing | 30 g |
| Sweet | 10 g |
| Bar | 75 g |
| Meal replacer drink | 330 ml |
| Beverages | 200 |

The use of the invention can further encompass the use of Menaquinone in combination with other healthy components such as for example vitamins A, B, C, D, E, minerals such as calcium, potassium, magnesium, iron, copper, zinc, selenium and anti-oxidants such as tocopherols, polyphenols.

In a preferred embodiments compositions of the invention may comprise further ingredients which are believed to reduce or prevent osteoporosis. Examples of such ingredients are calcium, vitamin D, magnesium etc.

Products according to the invention may be prepared by any convenient way.

In a preferred embodiment products according to the invention are prepared whereby menaquinone is added to the food product such that the level of menaquinione is between 5 to 5000 µg per 100 g product.

In another preferred embodiment products according to the invention are prepared whereby menaquinone is added to the food product to obtain a level 5 to 5000 µg of menaquinone per serving.

Unlike a number of natural products with vitamin K2, products according to the invention may advantageously be heat-treated without negatively impacting on taste, quality and stability of the vitamin K2 component.

Accordingly in a preferred embodiment the invention relates to the preparation of a food product according to the invention, whereby part or all of the food product containing the K2 ingredient is heat treated e.g. for cooking, baking, pasteurisation or sterilisation.

Products according to the invention may be used for promoting health of human beings, in particular for maintaining, strengthening or promoting bone or cardiovascular health. Preferably products according to the invention may suitably be used for the prevention or reduction of osteoporosis.

The invention will now be further illustrated by the description of suitable embodiments of the preferred food products for use in the invention. It is believed to be well within the ability of the skilled person to use the teaching provided therewith to prepare other products of the invention.

Margarines and Other Spreads

Typically these are oil in water or water in oil emulsions, also spreads which are substantially fat free are covered. Typically these products are spreadable and not pourable at the temperature of use e.g. 2-10° C. Fat levels may vary in a wide range e.g. full fat margarines with 60-90 wt % of fat, medium fat margarines with 30-60 wt % of fat, low fat products with 10-30 wt % of fat and very low or fat free margarines with 0 to 10 wt % of fat.

The fat in the margarine or other spread may be any edible fat, often used are soybean fat, rapeseed oil, sunflower oil and palm oil. Fats may be used as such or in modified form e.g. hydrogenated, esterified, refined etc. Other suitable oils are well known in the art and may be selected as desired.

It will be apparent that menaquinone when used in margarines or other spreads advantageously form part or all of the fat phase in said products.

Examples of spreads other than margarines are cheese spreads, sweet spreads etc. Butter is not a preferred spread according to the invention.

Optional further ingredients of spreads may be emulsifiers, colorants, vitamins, preservatives, emulsifiers, gums, thickeners etc. The balance of the product will normally be water.

A typical size for an average serving of margarine or other spreads is 14 g. Preferred Menaquinone levels in the margarine or spread are from 60 to 600 µg per serving, more preferred 75 to 400 µg, most preferred 100 to 200 µg per serving.

Frozen Confectionery Products

For the purpose of the invention the term frozen confectionery product includes milk containing frozen confections such as ice-cream, frozen yoghurt, sherbet, sorbet, ice milk and frozen custard, water-ices, granitas and frozen fruit purees.

Preferably the level of solids in the frozen confection (e.g. sugar, fat, flavouring etc) is more than 3 wt %, more preferred from 10 to 70 wt %, for example 40 to 70 wt %.

Ice-cream will typically comprise 2 to 20 wt % of fat, 0 to 20 wt % of sweeteners, 2 to 20 wt % of non-fat milk components and optional components such as emulsifiers, stabilisers, preservatives, flavouring ingredients, vitamins, minerals, etc, the balance being water. Typically ice-cream will be aerated e.g. to an overrun of 20 to 400%, more general 40 to 200% and frozen to a temperature of from −2 to −200° C., more general −10 to −30° C. Ice-cream normally comprises calcium at a level of about 0.1 wt %.

A typical size of an average serving of frozen confectionery material is 66 g. Preferred menaquinone levels are from 60 to 5,000 μg per serving, preferred 60 to 600 μg per serving, more preferred 75 to 400 μg, most preferred 100 to 200 μg per serving.

The menaquinone may be encapsulated or combined with emulsifiers, detergents or other agents to ensure solubilisation and stabilisation of the substance in the product.

Beverages, for Example Tea Based Products or Meal Replacers

Vitamin K2 can advantageously be used to beverages for example fruit juice, soft drinks etc. A very advantageous beverage in accordance to the invention is a tea based product or a meal replacers drink. These products will be described in more detail herein below. It will be apparent that similar levels and compositions apply to other beverages comprising vitamin K2.

For the purpose of this invention the term tea based products refers to products containing tea or tea replacing herbal compositions e.g. tea-bags, leaf tea, herbal tea bags, herbal infusions, powdered tea, powdered herbal tea, ice-tea, ice herbal tea, carbonated ice tea, carbonated herbal infusions etc.

Typically some tea based products of the invention may need a preparation step shortly before consuming, e.g. the making of tea brew from tea-bags, leaf tea, herbal tea bags or herbal infusions or the solubilisation of powdered tea or powdered herbal tea. For these products it is preferred to adjust the level of menaquinone in the product such that one serving of the final product to be consumes has the desired levels of menaquinone as described above.

For ice-tea, ice herbal tea, carbonated ice tea, carbonated herbal infusions the typical size of one serving will be 200 ml or 200 g.

Meal replacer drinks are typically based on a liquid base which may for example be thickened by means of gums or fibers and whereto a cocktails of minerals and vitamins are added. The drink can be flavoured to the desired taste e.g. fruit or choco flavour. A typical serving size may be 330 ml or 330 g.

Both for tea based beverages and for meal replacer drinks, preferred menaquinone levels are from 60 to 1,000 μg per serving, preferred 60 to 600 μg per serving, more preferred 75 to 400 μg, most preferred 100 to 200 μg per serving.

The menaquinone may be encapsulated or combined with emulsifiers, detergents or other agents to ensure solubilisation and stabilisation of the substance in the beverage.

For products which are extracted to obtain the final product, generally the aim is to ensure that one serving of 200 ml or 200 g comprises the desired amounts as indicated above. In this context it should be appreciated than normally only part of the Menaquinone present in the tea based product to be extracted will eventually be extracted into the final tea drink. To compensate for this effect generally it is desirable to incorporate into the products to be extracted about 2 times the amount of vitamin K2 as is desired to have in the extract.

For leaf tea or tea-bags typically 1-5 g of tea would be used to prepare a single serving of 200 ml. Preferred levels of vitamin K2 in the tea compound of such products would be from 60 to 5,000 μg per serving, preferred 60 to 600 μg per serving, more preferred 75 to 400 μg.

If tea-bags are used, the Menaquinone may advantageously be incorporated into the tea component. However it will be appreciated that for some applications it may be advantageous to separate the Menaquinone from the tea, for example by incorporating it into a separate compartment of the tea bag or applying it onto the tea-bag paper.

Salad Dressings or Mayonnaise

Generally dressings or mayonnaise are oil in water emulsions, The oil phase of the emulsion generally is 0 to 80 wt % of the product. For non fat reduced products the level of fat is typically from 60 to 80%, for salad dressings the level of fat is generally 10-60 wt %, more preferred 15-40 wt %, low or no fat dressings may for example contain triglyceride levels of 0, 5, 10, 15% by weight.

Dressings and mayonnaise are generally low pH products having a preferred pH of from 2-6.

Dressings or mayonnaise optionally may contain other ingredients such as emulsifiers (for example egg-yolk), stabilisers, acidifiers, biopolymers, bulking agents, flavours, coloring agents etc. The balance of the composition is water which could advantageously be present at a level of 0.1 to 99.9 wt %, more general 20-99 wt %, most preferred 50 to 98 wt %.

A typical size for an average serving of dressings or mayonnaise is 30 g. Preferred levels of vitamin K2 in such products would be from 60 to 5,000 μg per serving, preferred 60 to 600 μg per serving, more preferred 75 to 400 μg.

The menaquinone may be encapsulated or combined with emulsifiers, detergents or other agents to ensure solubilisation and stabilisation of the substance.

Meal Replacer Snacks or Bars

These products often comprise a matrix of edible material wherein the menaquinone can be incorporated. For example the matrix may be fat based (e.g. couverture or chocolate) or may be based on bakery products (bread, dough, cookies etc) or may be based on agglomerated particles (rice, grain, nuts, raisins, fruit particles).

A typical size for a snack or meal replacement bar could be from 20 to 200 g, generally from 40 to 100 g. Preferred levels of vitamin K2 in such products would be from 60 to 5,000 μg per serving, preferred 60 to 600 μg per serving, more preferred 75 to 400 μg.

Further ingredients may be added to the product such as flavouring materials, vitamins, minerals etc.

The invention will be further illustrated in the examples.

Example I

Bar 75 g of dark chocolate are melted at 70° C. and subsequently mixed with 600 μg of menaquinone (MK-4). The mixture is poured into a bar shaped mold and cooled overnight.

Example II

Milkshake 100 ml of vanilla flavoured ice-cream are mixed with 100 ml of cooled milk, 10 ml of strawberry syrup and 750 μg of menaquinone (MK-4). The mixture is fed through a blender and immediately served.

Example III

Nougat Bar

| Ingredient | weight (g) |
|---|---|
| Water | 70 |
| Hyfoama (emulsifier) | 3.5 |
| Gelatin | 2.0 |
| Sugar | 515 |
| Glucose syrup 60DE | 250 |
| Glucose syrup 35DE | 250 |
| Skimmed milk powder | 115 |
| Vitamin K2 (MKn) | 2 |
| Fat | 50 |

Method of preparation: dissolve hyfoama and gelatin in water add 150 g of sugar and beat to foam, heat remaining sugar to 130° C. and add slowly to foam. Add fat, glucose syrup, milkpowder and vitamin K2. Allow to cool and divide in bars of 50 g.

The invention claimed is:

1. A method for promoting cardiovascular health, comprising providing a food product which is not an egg, the food product containing vitamin K, wherein the total amount of vitamin K in the food product predominantly comprises menaquinone in an amount of 50 to 200 mcg per 100 g of product, with the proviso that if the menaquinone is a MK-n menaquinone, wherein n≧4, then the food product is not a cheese or natto.

2. A method according to claim 1 wherein the food product is not a highly proteinaceous food product such as meat, fish, or dairy product.

3. A method according to claim 1, wherein the food product is selected from the group of meal replacers, dietary supplements, ice-cream, sauces, dressing, spreads, bars, sweets, snacks, cereals and beverages.

4. A method according to claim 1 wherein the menaquinone level is from 50 to 100 mcg per 100 g product.

5. A method according to claim 1 wherein the menaquinone is a MK-4 menaquinone.

6. A method according to claim 1 further comprising one or more of calcium, vitamin D, or magnesium.

7. A method for promoting cardiovascular health, comprising providing a food product which is not an egg, cheese or natto, and adding vitamin K to the food product so that the total amount of vitamin K in the food product consists essentially of menaquinone in an amount of 50 to 200 mcg per 100 g of product.

8. A method for promoting cardiovascular health, comprising providing a food product containing vitamin K, wherein the food product is selected from the group of meal replacers, dietary supplements, ice-cream, sauces, dressing, margarine, bars, sweets, snacks, cereals and beverages, and the total amount of vitamin K in the food product consists essentially of menaquinone at a level of 50 to 200 mcg per serving.

9. A method according to claim 8 wherein the menaquinone level is from 50 to 100 mcg per serving.

10. A method according to claim 8 wherein the menaquinone is a MK-4 menaquinone.

11. A method according to claim 8 further comprising one or more of calcium, vitamin D, or magnesium.

12. A method for promoting cardiovascular health, comprising providing a food product containing vitamin K, wherein the food product is selected from the group of meal replacers, dietary supplements, ice-cream, sauces, dressing, margarine, bars, sweets, snacks, cereals and beverages, and adding an amount of vitamin K2 to the food product so that the total amount of vitamin K in the food product consists essentially of menaquinone at a level of 50 to 200 mcg per serving.

13. A method for promoting cardiovascular health of an individual comprising providing a food product containing vitamin K, wherein the total amount of vitamin K in the food product consists only of 50 to 200 mcg of menaquinone.

14. A method for promoting cardiovascular health of an individual according to claim 13, wherein the food product contains 50 mcg of menaquinone and is consumed once daily by the individual.

15. A method for promoting cardiovascular health according to claim 13, wherein the food product consists of 50 to 200 mcg of menaquinone per 100 grams of product or per serving and is consumed once daily by the individual.

16. A method for promoting cardiovascular health of an individual comprising providing a food product that does not contain vitamin K, and incorporating 50 to 200 mcg of menaquinone into the food product so that the food product contains only vitamin K2 as the source of vitamin K.

17. A method for promoting cardiovascular health of an individual comprising providing a food product that does not contain vitamin K, and incorporating 5 to 200 mcg of menaquinone into the food product so that the food product contains only vitamin K2 as the source of vitamin K.

18. A method for promoting cardiovascular health, comprising providing a food product which his not an egg, natto, or cheese, the food product containing vitamin K, wherein the total amount of vitamin K in the food product predominantly comprises menaquinone in an amount of 5 to 200 mcg 100 g of product.

* * * * *